(12) United States Patent
Ramji

(10) Patent No.: US 12,000,826 B2
(45) Date of Patent: Jun. 4, 2024

(54) METHODS FOR TESTING FOR FOOD ALLERGIES AND ALLERGENS IN FOODS

(71) Applicant: Anant Ramji, Mason, OH (US)

(72) Inventor: Anant Ramji, Mason, OH (US)

( * ) Notice: Subject to any disclaimer, the term of this patent is extended or adjusted under 35 U.S.C. 154(b) by 702 days.

(21) Appl. No.: 17/055,163

(22) PCT Filed: May 10, 2019

(86) PCT No.: PCT/US2019/031710
§ 371 (c)(1),
(2) Date: Nov. 13, 2020

(87) PCT Pub. No.: WO2019/226361
PCT Pub. Date: Nov. 28, 2019

(65) Prior Publication Data
US 2021/0199645 A1     Jul. 1, 2021

Related U.S. Application Data

(60) Provisional application No. 62/676,819, filed on May 25, 2018.

(51) Int. Cl.
*G01N 33/50*     (2006.01)
*G01N 21/64*     (2006.01)
*G01N 33/02*     (2006.01)

(52) U.S. Cl.
CPC ..... *G01N 33/5091* (2013.01); *G01N 21/6428* (2013.01); *G01N 33/02* (2013.01); *G01N 2021/6432* (2013.01); *G01N 2800/24* (2013.01)

(58) Field of Classification Search
CPC .............. G01N 33/02; G01N 33/5091; G01N 21/6428; G01N 2021/6432; G01N 2800/24
See application file for complete search history.

(56) References Cited

U.S. PATENT DOCUMENTS 6,818,181 B2   11/2004   Lee
6,858,398 B2   2/2005   Vojdani
(Continued)

OTHER PUBLICATIONS

Ferreira, Rosana Rossi, et al. "Characteristics of the histamine release from hamster cheek pouch mast cells stimulated by lectins from Brazilian beans and concanavalin A." Inflammation Research 45 (1996): 442-447. (Year: 1996).*

(Continued)

*Primary Examiner* — Robert J Eom
(74) *Attorney, Agent, or Firm* — Jenei LLC

(57) ABSTRACT

The present invention provides for methods and compositions for detecting the presence of a food allergy or food intolerance in a subject. In one aspect, the present invention provides for methods and compositions for detecting the presence of a food allergy or food intolerance in a subject without risk of adverse reactions in the test subject. Furthermore, if a subject has multiple allergies, a single test can determine if there is any allergic component in a food composition or mixture, as opposed to doing multiple individual test for each allergen. In an additional aspect, the present invention provides for methods that do not require identification of any particular allergen of interest. In one or more embodiments, a single test can determine if there is any allergic component in a food composition or mixture without needed to identify the particular allergen itself.

11 Claims, 8 Drawing Sheets

(56) References Cited

U.S. PATENT DOCUMENTS

| | | |
|---|---|---|
| 8,309,318 B2 | 11/2012 | Dorval et al. |
| 8,361,460 B2 | 1/2013 | Morimatsu |
| 2003/0143627 A1 | 7/2003 | Vojdani |
| 2009/0110601 A1 | 4/2009 | Levi et al. |
| 2009/0253154 A1 | 10/2009 | Vojdani |
| 2010/0210033 A1 | 8/2010 | Scott |
| 2017/0241994 A1 | 8/2017 | Paolicchi et al. |
| 2018/0289692 A1 | 10/2018 | Horan |

OTHER PUBLICATIONS

Seto, Daisuke, et al. "Selective fluorescence detection of histamine based on ligand exchange mechanism and its application to biomonitoring." Analytical biochemistry 404.2 (2010): 135-139. (Year: 2010).*

Barthow, Christine, et al. "The Probiotics in Pregnancy Study (PiP Study): rationale and design of a double-blind randomised controlled trial to improve maternal health during pregnancy and prevent infant eczema and allergy." BMC Pregnancy and Childbirth 16.1 (2016): 1-14. (Year: 2016).*

Wen, H., Borejsza-Wysocki, W., Decory, T. R., & Durst, R. A. (2007). Peanut Allergy, Peanut Allergens, and Methods for the Detection of Peanut Contamination in Food Products. Comprehensive Reviews in Food Science and Food Safety, 6(2), 47-58. doi:10.1111/j.1541-4337.2007.00017.x.

Matchar, E. (Sep. 9, 2015). Test Your Restaurant Meal for Allergens in Two Minutes. Retrieved from https://www.smithsonianmag.com/innovation/test-your-restaurant-meal-allergens-two-minutes-180956529/ Accessed Nov. 10, 2020.

Raithel, M. (2006). Colorectal mucosal histamine release by mucosa oxygenation in comparison with other established clinical tests in patients with gastrointestinally mediated allergy. World Journal of Gastroenterology, 12(29), 4699. doi:10.3748/wjg.v12.i29.4699.

Ferreira, R.R., Cavada, B.S., Moreira, R.A. et al. Characteristics of the histamine release from hamster cheek pouch mast cells stimulated by lectins from Brazilian beans and concanavalin A. Inflamm Res 45, 442-447 (1996). https://doi.org/10.1007/BF02252314.

* cited by examiner

METHODS FOR TESTING FOR FOOD ALLERGIES AND ALLERGENS IN FOODS

BACKGROUND OF THE INVENTION

1. Field of the Invention

The field of art disclosed herein pertains to methods and compositions for detecting the presence of a food allergy or food intolerance in a subject.

DESCRIPTION OF THE RELATED ART

In the developed world, about 4% to 8% of people have at least one food-related allergy and roughly 30,000 individuals require emergency room treatment as a result of food allergies. Food-related allergies cause a variety of illnesses, whether it be in humans or other animals. At present, there is no cure for food allergies and a food allergic consumer must avoid the food to which the consumer is allergic. The timing and location of an allergic reaction to food is affected by the digestive process.

An allergy is an immune malfunction wherein an individual is hypersensitized to react immunologically to typically per se harmless substances called allergens. The principal antibody which is involved in allergic reactions is IgE. The constant region (Fc region) of IgE is able to bind to specific receptors of cells, which are able to release histamine or other inflammatory mediators, cytokines and/or proteases into the surrounding tissue. Histamine releasing cells are mainly mast and basophilic cells. The release of histamine is initiated when cell-bound IgE is contacted and cross-linked by the allergen.

Histamine, which is stored mainly in mast cells and basophils, is a prominent contributor to allergic disease. Elevations in plasma or tissue histamine levels have been noted during anaphylaxis and experimental allergic responses of the skin, nose, and airways. Histamine released in the nose, eyes, and sinuses, for example, stimulates sneezing, a runny nose, and itchy eyes; released in the lungs it causes narrowing and swelling of the lining of the airways and the secretion of thick mucus; in the skin, rashes and hives; and in the digestive system, stomach cramps and diarrhea.

Typical allergens are derived from plant pollens, like rye grass, ragweed, timothy grass and birch trees pollens, mold spores, drugs, like penicillins, sulfonamides, salicylates and local anesthetics, foods, like nuts, seafood, egg, peas, beans, peanuts and other legumes, milk, insect products, like bee-sting venom, wasp sting venom, cockroach calyx and dust mites, and animal hair and dander.

A food allergy is an abnormal immune response to food. The signs and symptoms may range from mild to severe. They may include itchiness, swelling of the tongue, vomiting, diarrhea, hives, trouble breathing, or low blood pressure. This typically occurs within minutes to several hours of exposure. When the symptoms are severe, it is known as anaphylaxis.

Although sensitivity levels vary by country, the most common food allergies are allergies to milk, eggs, peanuts, tree nuts, seafood, shellfish, soy, and wheat. One of the most common food allergies is a sensitivity to peanuts, a member of the bean family. Peanut allergies may be severe, but children with peanut allergies sometimes outgrow them. Tree nuts, including cashews, Brazil nuts, hazelnuts, macadamia nuts, pecans, pistachios, pine nuts, coconuts, and walnuts, are also common allergens. Sufferers may be sensitive to one particular tree nut or to many different ones. Also, seeds, including sesame seeds and poppy seeds, contain oils where protein is present, which may elicit an allergic reaction.

Diagnosis is usually based on a medical history, elimination diet, skin prick test, blood tests for food-specific IgE antibodies, or oral food challenge.

For skin-prick tests, a tiny board with protruding needles is used. The allergens are placed either on the board or directly on the skin. The board is then placed on the skin, to puncture the skin and for the allergens to enter the body. If a hive appears, the person is considered positive for the allergy. This test only works for IgE antibodies. Allergic reactions caused by other antibodies cannot be detected through skin-prick tests. Patch testing is used to determine if a specific substance causes allergic inflammation of the skin. It tests for delayed food reactions.

Blood testing is another way to test for allergies; however, it poses the same disadvantage and only detects IgE allergens and does not work for every possible allergen.

Food challenges test for allergens other than those caused by IgE allergens. The allergen is given to the person in the form of a pill, so the person can ingest the allergen directly. The person is watched for signs and symptoms. The problem with food challenges is that they must be performed in the hospital under careful watch, due to the possibility of anaphylaxis.

For tests that involve a reaction of the subjects themselves, subjects cannot be administered many different tests in a short period of time. In addition, these types of tests are expensive and invasive.

Additional diagnostic tools for evaluation of eosinophilic or non-IgE antibody mediated reactions include endoscopy, colonoscopy, and biopsy.

U.S. Pat. No. 6,858,398 describes a saliva test for detection of food allergy and Intolerance. This patent describes determination of antibodies against a dietary antigen in mucosal sample of patients with food allergies. The method uses IgA and IgM against specific foods using saliva of subjects and is detected in a reaction with antigen immobilized on a solid support using ELISA.

U.S. Pat. No. 8,361,460 describes methods of detecting food allergens and methods of detecting food allergy-inducing foods. The patent describes detection of allergens in food by reaction of IgE antibodies isolated from pooled serum of food allergy patients with the allergens in food. The antigens of this invention are native or heated food allergens that IgE antibodies of food allergy patients recognize. The antibodies were prepared by immunizing animals with above antigen. The food allergy detection method relates to the mentioned antibodies.

U.S. Pat. No. 6,818,181 describes a kit and method for detecting food allergies. The invention concerns a home kit and a method for detection of food allergies by determining the presence of antibodies against specific antigen in stool samples.

US Patent Publ. No. US 2010/0210033 describes a portable device for detecting food allergens.

There is now a need for quick, accurate, simple assays that can be performed by laboratory personnel as well as by non-technical personnel outside of a laboratory setting to test biological fluids of organisms to determine the presence of food, food additive or chemical allergies.

SUMMARY OF THE INVENTION

In one aspect, the present disclosure provides for methods and compositions for detecting the presence of a food allergy or food intolerance in a subject.

Therefore, it is an object of the present invention to provide in vitro means and methods to monitor a possible allergen sensitivity of an individual subject.

In an additional aspect, the present innovation provides for methods and compositions for detecting the presence of a food allergy or food intolerance in a subject without risk of adverse reactions in the test subject.

The present invention provides for a simple and rapid test that will accurately inform a physician of clinical conditions used to diagnose patients who may suffer from food allergies or food intolerance. The test utilizes an ex vivo method that measures a histamine response from mast cells in response to known dietary antigens that are presented in the test.

The present invention is not specific to the allergen being tested and can be performed in a very short amount of time. The methods of the present invention can be used in conjunction with any allergen or suspected allergen to be tested and can be performed in a very short amount of time. In one or more embodiments, the reaction of allergen with buccal cells produces an immediate histamine production and release that can be detected. The methods are inexpensive, very sensitive in detection, and can provide a non-invasive option for in-office or at-home testing for food allergies. Furthermore, if a subject has multiple allergies, a single test can determine if there is any allergic component in a food composition or mixture, as opposed to doing multiple individual test for each allergen. In one or more embodiments, the methods do not require identification of any particular allergen of interest. Any food substance can be tested. In one or more embodiments, a single test can determine if there is any allergic component in a food composition or mixture without needed to identify the particular allergen itself. All that is necessary is that a response to the food composition shows a reaction and the test subject thereby is informed to avoid the particular food composition or mixture.

Most commercially available test kits have antibodies to specific food antigen that can be detected as a color change or other methods. These antibodies are many times nonspecific as an individual with food allergies are allergic to various allergic components in a food. Further, an individual could be allergic to multiple foods, e.g., eggs and nuts. It would not be practical to run all possible tests at the moment that the food is presented to an individual with food allergies. The present invention makes use of cheek cells from an individual in a quick test to detect a reaction to an allergen. Further, the cheek cells from an individual who has food allergy has all the elements necessary in order to trigger a response to any allergen present in the food to which the individual may have an allergic reaction. In one or more embodiments, the cheek cells are buccal cells. In one or more embodiments, the buccal cells comprise mast cells. Mast cells (MCs) are resident cells of several types of tissues and contain many granules rich in histamine and heparin. They are distributed preferentially about the micro-vascular endothelial cells in the oral (buccal) mucosa.

Histamine is produced by the reaction of the allergen with mast cells present in the cheek cells (ex vivo) and the histamine that was produced was detected by use of a fluorescent tag or probe. Testing for an allergy in a quick test without involving the subject (in vivo) is one of the critical aspects of this invention.

The present invention provides for obtaining buccal cells, e.g., those obtained from an oral swab of an individual having food allergy, and combining them with a filtered extract of an allergen or a food containing a suspected allergen in the presence of a dye for the detection of histamine produced to indicate if the allergen presented will cause an allergic response in the individual.

The buccal mucosa cells (non-cornified squamous epithelial cells lining the inside of the cheek) from subjects can be easily and safely obtained, e.g., by using a swab or brush (or other collection device such as a toothbrush), and maintained in culture which allows further analysis in the cells. Thus, the present invention includes methods for the diagnosis of an allergic reaction that include obtaining a sample comprising buccal cells, contacting the sample with a fluorescent dye or indicator in order to indicate the presence of or risk of an allergic reaction.

In addition, the cheek cells are very stable in phosphate buffer when refrigerated (e.g., over a period of 10 days or more) and therefore can be collected and used at a convenient time after collection.

In one or more embodiments, the test involves using a method for detecting food allergies and food intolerance in a subject. In one or more embodiments, the method includes (a) determining a level of a histamine response from mast cells in response to dietary antigens in epithelial cells from the patient; and (b) comparing the level determined in step (a) with normal levels of histamine in samples.

In one or more embodiments, the method includes (a) identifying a subject in need of testing; (b) obtaining epithelial cells by a buccal (cheek) swab of the identified test subject; (c) contacting the isolated cheek cells with an allergen, antigen or food substance of interest; (d) determining a level of a histamine response from mast cells in response to the test allergen, antigen or food substance of interest in the isolated epithelial cells from the subject; and (e) comparing the level determined in step (d) with normal levels of histamine in samples.

The possible outcomes for the comparison include (i) lower than normal or about normal levels of histamine to dietary food antigens indicating optimal conditions; and (ii) higher than normal levels of histamine to dietary food antigens indicating a food allergy or food intolerance to one or more components of the tested substance.

In one or more embodiments, the method includes obtaining isolated cheek cells comprising cells capable of releasing histamine upon activation upon to exposure or contact with certain allergens or antigens. In one or more embodiments, the method includes obtaining isolated cheek cells comprising basophils or mast cells.

In one or more embodiments, the method includes measuring the release of histamine and other mast cell or basophil products, which are released upon allergen activation of the mast cells and basophils.

In one or more embodiments, the method utilizes a fluorescent probe or dye for monitoring the release of histamine and other mast cell or basophil products, which are released upon allergen activation of the mast cells and basophils.

In one or more embodiments, the method utilizes a fluorescent probe, a complex between $Ni^{2+}$ and calcein, based on a ligand exchange mechanism. The fluorescence intensity of this probe, which has been reduced due to effective quenching by $Ni^{2+}$ ion, increases drastically upon contact of histamine. Furthermore, the probe shows high selectivity toward histamine among the various neurotransmitters in 0.1M phosphate buffer solution (pH 7.4). See, for example, Seto, D., Soh, N., Nakano, K., & Imato, T. (2010). Selective fluorescence detection of histamine based on ligand exchange mechanism and its application to biomonitoring. *Analytical Biochemistry*, 404(2), 135-139.

In another aspect, the invention relates to a method for detecting the food allergens and food allergy-inducing foods that is applicable to foods containing the allergens without any restriction. Examples of the allergy-inducing foods are eggs, milk, meat, fishes, crustacea and mollusks, cereals, legumes and nuts, fruits, vegetables, beer yeast, and gelatin. More particularly, egg white and egg yolk of the eggs, milk and cheese of the milk, pork, beef, chicken and mutton of the meat, mackerel, horse mackerel, sardine, tuna, salmon, codfish, flatfish and salmon caviar of the fishes, crab, shrimp, blue mussel, squid, octopus, lobster and abalone of the crustacea and mollusks, wheat, rice, buckwheat, rye, barley, oat, corn, millet, foxtail millet and barnyardgrass of the cereals, soybean, peanut, cacao, pea, kidney bean, hazelnut, Brazil nut, almond, coconut and walnut of the legumes and nuts, apple, banana, orange, peach, kiwi, strawberry, melon, avocado, grapefruit, mango, pear, sesame and mustard of the fruits, tomato, carrot, potato, spinach, onion, garlic, bamboo shoot, pumpkin, sweet potato, celery, parsley, yam and Matsutake mushroom of the vegetables, the foods containing them, and the ingredients thereof (e.g., ovoalbumin, ovomucoid, lysozyme, casein, beta-lactoglobulin, alpha-lactoalbumin, gluten, and alpha-amylase inhibitor). These foods may be processed by heating, freezing, drying, salting, fermentation, enzymatic processing, etc.

According to another embodiment, the at least one allergen is a nut allergen. According to another embodiment, the at least one allergen is a peanut allergen. According to another embodiment, the at least one allergen is a tree nut allergen. According to another embodiment, the at least one allergen is a cashew allergen. According to another embodiment, the allergen is a food allergen. According to some such embodiments, the food allergen is an apple allergen. According to some such embodiments, the food allergen is a milk allergen. According to some such embodiments, the food allergen is a drug allergen. According to another embodiment, the allergen is an environmental allergen. According to some such embodiments, the environmental allergen is a cockroach allergen. According to another embodiment, the at least one allergen is a tree pollen allergen. According to another embodiment, the at least one allergen is a mold allergen. According to another embodiment, the at least one allergen is a hay allergen. According to another embodiment, the at least one allergen is a grass allergen.

In another aspect, the invention relates to methods, kits and apparatuses for the detection and determination of an immune response to allergens in foods, chemicals, and food additives.

In one or more embodiments, the present invention provides for a kit for evaluating the allergen sensitivity of an individual to at least one allergy comprising: at least two of the following components at least one allergen for inducing a histamine release of cells capable of releasing histamine in response to an allergen, means for detecting the histamine, at least one histamine standard, and a collection swab for buccal cells. In one or more embodiments, the cells are mast and/or basophilic and/or eosinophilic cells.

In one or more embodiments, the allergen is a food allergen.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE FIGURES

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
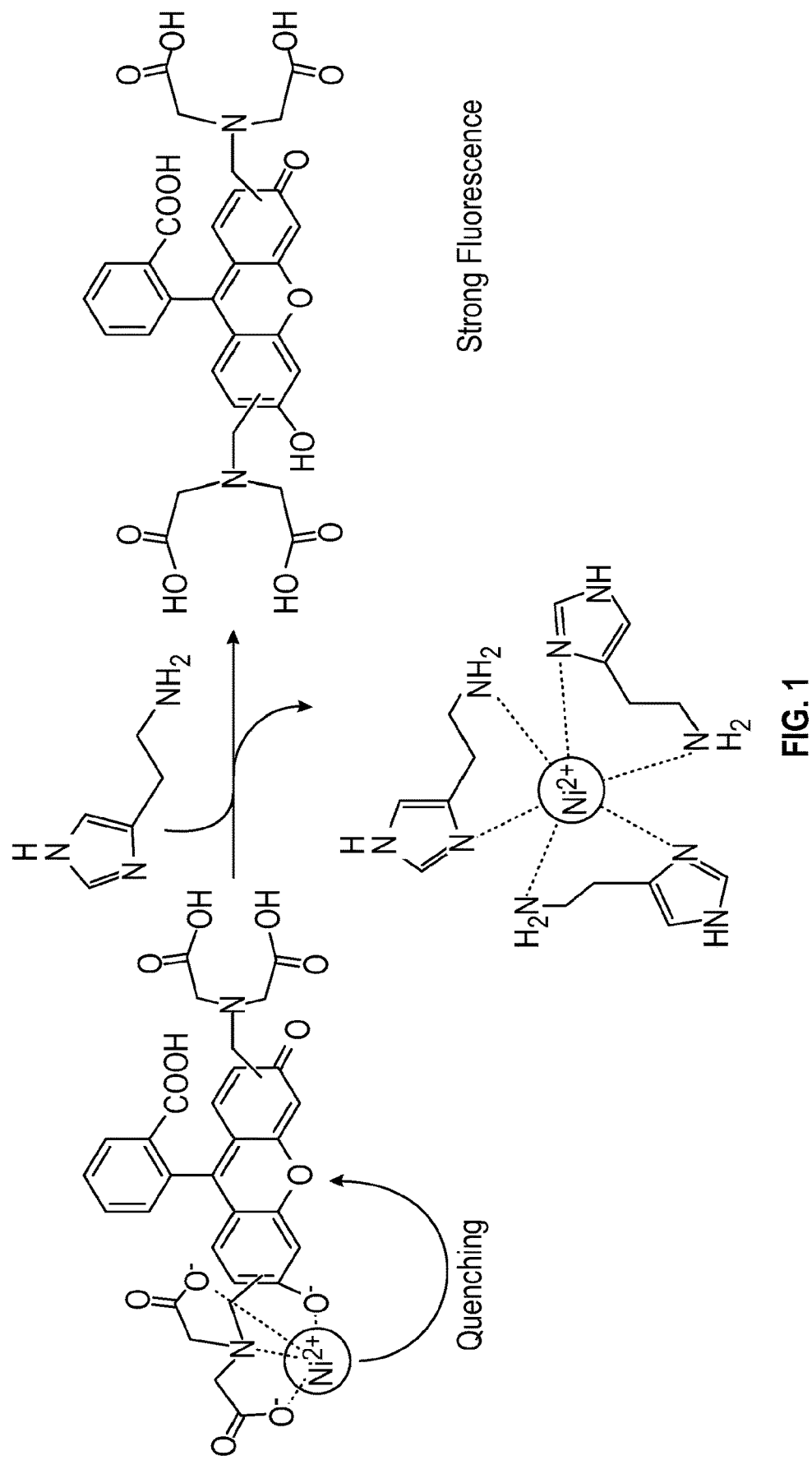
FIG. 1 illustrates the mechanism of histamine detection using new method for a fluorescent probe, a complex between $Ni^{2+}$ and calcein, based on a ligand exchange mechanism. The fluorescence intensity of the calcein probe, which is initially reduced due to quenching by $Ni^{2+}$ ions, increases upon addition of histamine.

Before describing the invention in detail, we will set out certain definitions as follows:

Definitions

"Allergens," as used herein, relate to substances that cause allergies. Allergens may be from food, chemicals or food additives. Structurally speaking, allergens may range in size from small and simple chemical compounds to polypeptides and other biological macromolecules.

The term "allergy" as used herein refers to an abnormal reaction of the body to a previously encountered allergen introduced by inhalation, ingestion or skin contact. The use of the term "allergy" also is inclusive of clinically adverse reactions to environmental antigens (allergens) which reflect the expression of acquired immunologic responsiveness involving allergen-specific antibodies and/or T cells. The term "allergy" includes adverse immunologic responses that are associated with the production and release of histamine by mast cells, which triggers allergy symptoms.

The term "allergic diseases" as used herein refers to the group of clinical disorders in which immune responses, typically directed against otherwise innocuous environmental allergens, are thought to have a pathogenetic role. Allergic diseases include, but are not limited to, hay fever, allergic asthma, atopic dermatitis, and clinical disorders in which IgE associated immune responses are thought to have a role.

The term "anaphylactic shock" as used herein refers to a sudden, severe allergic reaction typically characterized by a sharp drop in blood pressure, urticaria, and breathing difficulties that is caused by exposure to a foreign substance after a preliminary or sensitizing exposure. The term "anaphylaxis" as used herein refers to hypersensitivity to a substance that is caused by exposure to a foreign substance after a preliminary exposure.

The term "antigen" and its various grammatical forms refers to any substance that can stimulate the production of antibodies and can combine specifically with them. The term "antigenic determinant" or "epitope" as used herein refers to an antigenic site on a molecule.

"Basophils" are a type of white blood cells. Basophils are the least common of the granulocytes, representing about 0.5 to 1% of circulating white blood cells. However, they are the largest type of granulocyte. They are responsible for inflammatory reactions during immune response, as well as in the formation of acute and chronic allergic diseases, including anaphylaxis, asthma, atopic dermatitis and hay fever. They can perform phagocytosis (cell eating), produce histamine and serotonin that induce inflammation, and heparin that prevents blood clotting, although there are less than that found in Mast cell granules.

A "buccal swab," also known as buccal smear or cheek swab, is a way to collect cells on the inside of a subject's cheek. Buccal swabs are a relatively non-invasive way to collect cell samples for testing. Buccal means cheek or mouth.

The term "contact" and all its grammatical forms as used herein refers to a state or condition of touching or of immediate or local proximity.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreeni, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, Xrhodamine, Lissamine Rhodamine B, Texas Red, TruRed, and derivatives thereof.

"Dietary antigens" of one or more embodiments are classified into the general groups as followed: milk and milk products; eggs and egg products; meat and meat products; fish, mollusks, and crustaceans and their products; oils, fats, and their products; grains and grain products; pulses, seeds, kernels, nuts, and their products; vegetables and vegetable products; fruits and fruit products; sugar, sugar products, chocolate products, and confectionery; and spices and herbs.

"Eosinophils," sometimes called eosinophiles or, less commonly, acidophils, are a variety of white blood cells and one of the immune system components responsible for combating multicellular parasites and certain infections in vertebrates. Along with mast cells and basophils, they also control mechanisms associated with allergy and asthma. Eosinophils, along with basophils and mast cells, are important mediators of allergic responses and asthma pathogenesis and are associated with disease severity.

A fluorescent tag, also known as a label or probe, is a molecule that is attached chemically to aid in the labeling and detection of a biomolecule such as a protein, antibody, or amino acid. Generally, fluorescent tagging, or labeling, uses a reactive derivative of a fluorescent molecule known as a fluorophore. A fluorophore (or fluorochrome, similarly to a chromophore) is a fluorescent chemical compound that can re-emit light upon light excitation.

"Histamine" is an organic nitrogenous compound involved in local immune responses, as well as regulating physiological function in the gut and acting as a neurotransmitter for the brain, spinal cord, and uterus. Histamine is involved in the inflammatory response and has a central role as a mediator of itching. As part of an immune response to foreign pathogens, histamine is produced by basophils and by mast cells found in nearby connective tissues. Histamine increases the permeability of the capillaries to white blood cells and some proteins, to allow them to engage pathogens in the infected tissues. Histamine has two basic centers, namely the aliphatic amino group and whichever nitrogen atom of the imidazole ring does not already have a proton. Under physiological conditions, the aliphatic amino group (having a pKa around 9.4) will be protonated, whereas the second nitrogen of the imidazole ring (having a pKa around 5.8) will not be protonated. Thus, histamine is normally protonated to a singly charged cation. A "cation" is an ion with fewer electrons than protons, giving it a positive charge, i.e., one that would be attracted to the cathode in electrolysis.

A "mast cell" or "mast cells" (also known as a mastocyte or a labrocyte) is a type of white blood cell. Specifically, it is a type of granulocyte derived from the myeloid stem cell that is a part of the immune and neuroimmune systems and contains many granules rich in histamine and heparin. The mast cell is very similar in both appearance and function to the basophil, another type of white blood cell. Mast cells play a key role in the inflammatory process. When activated, a mast cell can either selectively release (piecemeal degranulation) or rapidly release (anaphylactic degranulation) "mediators", or compounds that induce inflammation, (e.g., histamine, tryptase, and serotonin) from storage granules into the local microenvironment. Mast cells can be stimulated to degranulate by allergens through cross-linking with immunoglobulin E receptors. In allergic reactions, mast cells remain inactive until an allergen binds to IgE already coated upon the cell.

The term "subject" or "individual" or "patient" are used interchangeably to refer to a member of an animal species of mammalian origin, including but not limited to, a mouse, a rat, a cat, a goat, sheep, horse, hamster, ferret, pig, a dog, a guinea pig, a platypus, a rabbit and a primate, such as, for example, a monkey, ape, or human.

The term "subject prone to allergy" as used herein means a subject having a medical history or previous allergic reaction to at least one allergen other than the allergen responsible for the allergy.

The term "susceptible" as used herein refers to a member of a population at risk. The term is inclusive of a subject having a medical history of a previous allergic reaction to at least one allergen and at risk of mounting an allergic reaction to a different antigen.

DESCRIPTION OF THE PREFERRED EMBODIMENTS

The present invention provides for a simple and rapid test that will accurately inform a physician of clinical conditions used to diagnose patients who may suffer from food allergies or food intolerance. The test utilizes a method that measures a histamine response from mast cells in response to dietary antigens.

The present invention provides for a simple and rapid test that will accurately inform a physician of clinical conditions used to diagnose patients who may suffer from food allergies or food intolerance. The test utilizes a method that measures a histamine response from mast cells in response to dietary antigens.

The test involves using a method for detecting food allergies and food intolerance in a subject. The method includes (a) determining a level of a histamine response from mast cells in response to dietary antigens in epithelial cells from the patient; and (b) comparing the level determined in step (a) with normal levels of histamine in samples.

In one or more embodiments, the method includes (a) identifying a subject in need of testing; (b) obtaining epithelial cells by a buccal (cheek) cell collection of the identified test subject; (c) contacting the isolated cheek cells with an allergen or antigen of interest; (d) determining a level of a histamine response from mast cells in response to the test allergen or antigen of interest in the isolated epithelial cells from the subject; and (e) comparing the level determined in step (d) with normal levels of histamine in samples.

The possible outcomes for the comparison include (i) lower than normal or about normal levels of histamine to dietary food antigens indicating optimal conditions; and (ii) higher than normal levels of histamine to dietary food antigens indicating a food allergy or food intolerance.

In one or more embodiments, the method includes obtaining isolated cheek cells comprise cells capable of releasing histamine upon activation upon to exposure or contact with certain allergens or antigens. In one or more embodiments, the method includes obtaining isolated cheek cells comprise basophils or mast cells.

In one or more embodiments, the method includes measuring the release of histamine and other mast cell or basophil products, which are released upon allergen activation of the mast cells and/or basophils.

In another aspect, the invention relates to a method for detecting the food allergens and food allergy-inducing foods that is applicable to foods containing the allergens without any restriction. Examples of the allergy-inducing foods are eggs, milk, meat, fishes, crustacea and mollusks, cereals, legumes and nuts, fruits, vegetables, beer yeast, and gelatin. More particularly, egg white and egg yolk of the eggs, milk and cheese of the milk, pork, beef, chicken and mutton of the meat, mackerel, horse mackerel, sardine, tuna, salmon, codfish, flatfish and salmon caviar of the fishes, crab, shrimp, blue mussel, squid, octopus, lobster and abalone of the crustacea and mollusks, wheat, rice, buckwheat, rye, barley, oat, corn, millet, foxtail millet and barnyardgrass of the cereals, soybean, peanut, cacao, pea, kidney bean, hazelnut, Brazil nut, almond, coconut and walnut of the legumes and nuts, apple, banana, orange, peach, kiwi, strawberry, melon, avocado, grapefruit, mango, pear, sesame and mustard of the fruits, tomato, carrot, potato, spinach, onion, garlic, bamboo shoot, pumpkin, sweet potato, celery, parsley, yam and Matsutake mushroom of the vegetables, the foods containing them, and the ingredients thereof (e.g., ovoalbumin, ovomucoid, lysozyme, casein, beta-lactoglobulin, alpha-lactoalbumin, gluten, and alpha-amylase inhibitor). These foods may be processed by heating, freezing, drying, salting, fermentation, enzymatic processing, etc.

According to another embodiment, the allergy to be detected by methods of the present invention is a food allergy, wherein the presentation of the food allergy is correlated to the level of production of histamine in mast cells and/or basophils. According to some such embodiments, the food allergy is a nut allergy. According to some such embodiments, the nut allergy is a peanut allergy. According to some such embodiments, the nut allergy is a tree nut allergy. According to some such embodiments, the nut allergy is a cashew allergy. According to some such embodiments, the food allergy is an apple allergy. According to some such embodiments, the food allergy is a milk allergy. According to some such embodiments, the allergy is an environmental allergy, wherein the presentation of the environmental allergy is correlated to the level of production of histamine in mast cells and basophils. According to some such embodiments, the environmental allergy is a cockroach allergen allergy. According to some such embodiments, the allergy is a drug allergy, wherein the presentation of the drug allergy is correlated to the level of production of histamine in mast cells and basophils. According to another embodiment, the allergy is a tree pollen allergy, wherein the presentation of the tree pollen allergy is correlated to the level of production of histamine in mast cells and basophils. According to another embodiment, the allergy is a mold allergy, wherein the presentation of the mold allergy is correlated to the level of production of histamine in mast cells and basophils. According to another embodiment, the allergy is a hay allergy, wherein the presentation of the hay allergy is correlated to the level of production of histamine in mast cells and basophils. According to another embodiment, the allergy is a grass allergy, wherein the presentation of the grass allergy is correlated to the level of production of histamine in mast cells and/or basophils.

In one or more embodiments, the method includes obtaining isolated cheek cells comprise cells capable of releasing histamine upon activation upon to exposure or contact with certain allergens or antigens. In one or more embodiments, the method includes obtaining isolated cheek cells comprising basophils and/or mast cells.

In one or more embodiments, the method includes measuring the release of histamine and other mast cell or basophil products, which are released upon allergen activation of the mast cells and/or basophils.

In one or more embodiments, the method utilizes a fluorescent probe or dye for monitoring the release of histamine and other mast cell or basophil products, which are released upon allergen activation of the mast cells and/or basophils.

Cell Collection Methods

The cell sample to be used in one or more methods according to the present invention may be a saliva or cheek cell sample. The collected cells used in the method according to the present invention may be isolated from the sample. Due to this isolation, other possibly interfering substances present in the sample may be removed. In one or more embodiments, the collected cells are mast and/or basophilic and/or eosinophilic cells.

There are three primary methods for collecting oral cell samples—dry, wet and non-invasive procedures.

Dry procedures require the subject to insert a cytobrush, buccal swabs or other collection device into the mouth where tissue is scraped from the gum and cheek surfaces. These methods collect primarily buccal cells. Wet procedures include swishing liquids in the mouth and spitting them into a collecting vessel. A liquid wash is typically used for this procedure. A completely non-invasive collection system is a simple, painless procedure that requires the donor to spit into a collection device. Typically, after providing a sample, a detection solution is added to mix with the cells or saliva. Subjects should refrain from eating or drinking for at least 60 min prior to each collection.

For brush or swab collection, a subject should 1) vigorously rinse his/her mouth with water for about 15 sec to remove food particles, and 2) rub one cytobrush (e.g., CytoSoft™ brush, Medical Packaging Corp., Camarillo, CA) or one foam swab (e.g., Puritan Medical Products Co., Guilford, ME) against his/her right cheek for 5-45 sec. Subjects should turn the swabs to utilize both sides of the swab. In order to maximize buccal cell yield, cytobrushes and swabs should be used immediately after collection.

For oral-rinse and whole-saliva collection, subjects should rub their tongues around the inside of their mouths for about 15 sec and to swish vigorously with about 10 ml of oral rinse for 5-45 sec. Subjects should expectorate the cells into a clean specimen cup. In one or more embodiments, the cells are used immediately after collection.

In one or more embodiments, whole saliva is collected.

In one or more embodiments, the subjects deposit approximately 2 ml saliva into the collection cup. When an adequate sample is collected, a histamine detection agent is added as a solution and mixes with the saliva. After color formation, the color is compared to a standard to determine if a histamine release occurred upon contact with the collected cells.

The sample is preferably contacted with varying concentrations of the allergen. The amount of histamine released from a histamine releasing cell depends on the concentration of the allergen employed in the method according to the present invention. According to one or more embodiments, the determination of the amount of histamine released requires the use of varying concentrations of allergen. According to one or more embodiments, the concentration of the allergen is selected within the range of 1 ng/ml to 100 µg/ml, preferably within the range of 1 pg/ml to 10 µg/ml. According to one or more embodiments, the total amount of histamine of the cells contained in the sample provided by an individual is determined.

Histamine Detection

In one or more embodiments, the histamine is detected using a dye or label. As used herein, the term "label" refers to any composition that can be used to generate the signals that constitute an indicium. The signals generated by a label can be of any form that can be resolved subsequently to constitute the indicium. Preferably, the signal is a light within the visible range. In some embodiments, the signal is a light not in the visible range. In some embodiments, the signal is a radio signal, an X-ray signal, or an electromagnetic signal. However, it will be understood by one of skill in the art that equipment and devices are available for recording and monitoring light of any wavelength.

In fluorescence assay technology, it is possible to detect fluorescence signals in a reaction. In applying the principle of fluorescence, the product exposed to or excited by a light source corresponding to a first wavelength will in turn emit light rays or fluorescence signals at a second wavelength. The first, excitation, wavelength generally varies in a range from 250 to 450 nm. The second, emission, wavelength, for its part, is located in an emission range located between 300 and 600 nm.

Thus, the detection of fluorescence signals (in relative fluorescence units) combined with a treatment of the signal of these fluorescence signals originating from the reaction medium, itself originating from the sample to be tested and containing the reaction products, makes it possible to determine, for example, the presence or the concentration of the analyte of interest sought within the sample.

In some embodiments, the dye or label is a fluorescent compound. In some embodiments, the fluorescent compound can be, for example, fluorescein, rhodamine, Alexa Fluors, DyLight fluors, ATTO Dyes, or any analogs or derivatives thereof. In some embodiments, the fluorescent label can be, for example, fluorescein and chemical derivatives thereof, Eosin, Carboxyfluorescein, Fluorescein isothiocyanate (FITC), Fluorescein amidite (FAM), Erythrosine, Rose Bengal, fluorescein secreted from the bacterium *Pseudomonas aeruginosa*, Methylene blue, Laser dyes, Rhodamine dyes, Rhodamine, Rhodamine 6G, Rhodamine B, Rhodamine 123, Auramine O, Sulforhodamine 101, Sulforhodamine B, Texas Red, ATTO dyes, Acridine dyes, Acridine orange, Acridine yellow, Alexa Fluor, 7-Aminoactinomycin D, 8-Anilinonaphthalene-1-sulfonate, Auramine-rhodamine stain, Benzanthrone, 5,12-Bis(phenylethynyl) naphthacene, 9,10-Bis(phenylethynyl)anthracene, Blacklight paint, Brainbow, Calcein, Carboxyfluorescein, Carboxyfluorescein diacetate succinimidyl ester, Carboxyfluorescein succinimidyl ester, 1-Chloro-9,10-bis(phenylethynyl)anthracene, 2-Chloro-9,10-bis(phenylethynyl) anthracene, 2-Chloro-9,10-diphenylanthracene, Coumarin, Cyanine dyes, Cy3, Cy5, Cy5.5, DiOC6, SYBR Green I, DAPI, Dark quencher, DyLight Fluor, Fluo-4, FluoProbes, Fluorone dyes, Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin, Fluoro-Jade stain, Fura-2, Fura-2-acetoxymethyl ester, Green fluorescent protein, Hoechst stain, Indian yellow, Indo-1, Lucifer yellow, Luciferin, Merocyanine, Optical brightener, Oxazin dyes, Cresyl violet, Nile blue, Nile red), Perylene, Phenanthridine dyes, Ethidium bromide, Propidium iodide, Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), TSQ, Umbelliferone, or Yellow fluorescent protein.

In some embodiments, the signals emitted from labels comprise a light at a wavelength in the visible range. In some embodiments, the signals emitted from labels comprise lights of different wavelengths in the visible range.

In one or more embodiments, the method utilizes a fluorescent probe, a complex between $Ni^{2+}$ and calcein, based on a ligand exchange mechanism. The fluorescence intensity of this probe, which has been reduced due to effective quenching by Ni$^{2+}$ ion, increases drastically upon contact of histamine. Furthermore, the probe shows high selectivity toward histamine among the various neurotransmitters in 0.1 M phosphate buffer solution (pH 7.4). See, for example, Seto, D., Soh, N., Nakano, K., & Imato, T. (2010). Selective fluorescence detection of histamine based on ligand exchange mechanism and its application to biomonitoring. *Analytical Biochemistry*, 404(2), 135-139.

In one or more embodiments, the invention relates to a composition for fluorescence assay comprising a quenched fluorogenic compound forming a fluorescent compound after release of a bound group. "Quenched fluorogenic compound" is intended to mean a compound containing a group that, when it comprises this group bound, is incapable of emitting fluorescence ("fluorescence quenching"), but which emits a fluorescent signal when the group is separated from the compound. This may be referred to as a "quenching" group.

As examples of such quenched fluorogenic compounds, mention may be made of derivatives of fluorescent compounds that are customary for those skilled in the art, such as coumarin or resorufin derivatives, which contain groups that prevent the emission of fluorescence. By way of example of such groups, mention may be made of the group —C(O)—CH3 which, if bound to resorufin, quenches the fluorescence of resorufin. A resorufin derivative comprising such a group is the reagent Amplex Red, the group loss mechanism of which, to produce fluorescent resorufin in the presence of inorganic phosphate (indirect reaction), is described in the PiPer Phosphate Assay kit (Invitrogen) manual.

Other examples of quenched fluorescent compounds that may be used for the purposes of the invention comprise selective chemosensors associated with a cation, which are quenched in this associated form. They are referred to as quenched chemosensor-cation complexes.

Byway of nonlimiting example of a chemosensor that may be used, the following fluorescent compounds may be mentioned:

(i) hydrophilic coumarins, as described by Jung H. S. et al., 2009, Thomas F. and Serratrice G., 1999, and Yao J. et al., 2009, such as: 7-(diethylamino)-2-oxo-N-((pyridin-2-yl)-methyl)-2H-chromene-3-car-boxamide:

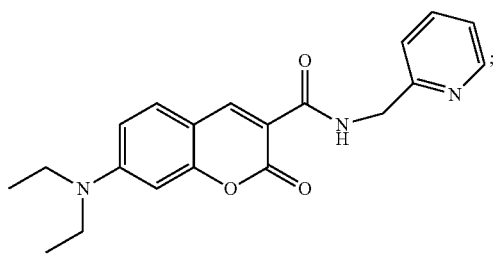 [SMILES: CCN(CC)c1ccc2cc(C(=O)NCc3ccccn3)c(=O)oc2c1]

N-(1,3-dihydroxy-2-(hydroxymethyl)propan-2-yl)-2-oxo-2H-chromene-3-carbox-amide

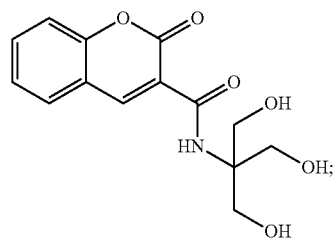 [SMILES: O=C(NC(CO)(CO)CO)c1cc2ccccc2oc1=O]

calcein:

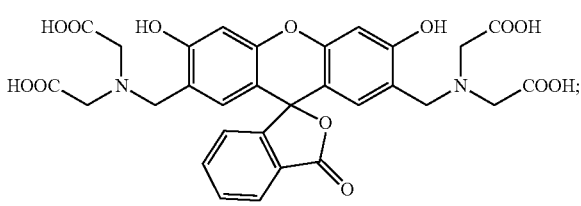 [SMILES: O=C(O)CN(CC(=O)O)Cc1cc2c(cc1O)Oc1cc(O)c(CN(CC(=O)O)CC(=O)O)cc1C21OC(=O)c2ccccc21]

and calcein blue:

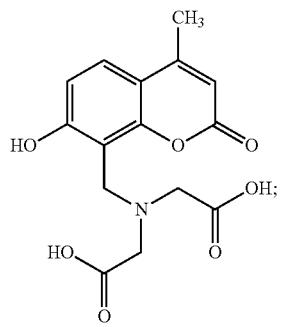 [SMILES: Cc1cc(=O)oc2c(CN(CC(=O)O)CC(=O)O)c(O)ccc12]

(ii) poly(9-aminofluorene), as described in Zhang G. et al., 2012; (iii) benzimidazole derivatives, as described by Alvaro M. et al., 2001, Henary M. M. et al., 2004 and Saluja P. et al., 2012, such as: N-[2-(1H-benzo[d]imidazol-2-yl)-phenyl]-N-[(E)-1-(1H-pyrrol-2-yl)methylid-ene]amine of following formula (I):

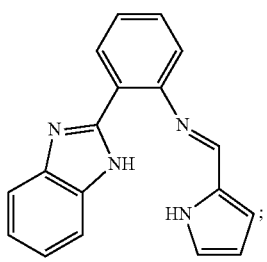

the N,S,-macrocycle of bis-benzimidazole derivative; {4-[2-(1H-benzimidazol-2-yl)phenyl-sulfamoyl]-phenoxy} acetic acid:

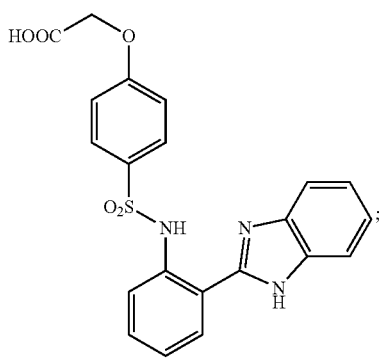 [SMILES: O=C(O)COc1ccc(S(=O)(=O)Nc2ccccc2-c2nc3ccccc3[nH]2)cc1]

{4-{2-{4-[(diethylamino)methyl]-1H-benzimidazol-2-yl}phenyl-sulfamoyl}phe-noxy} acetic acid:

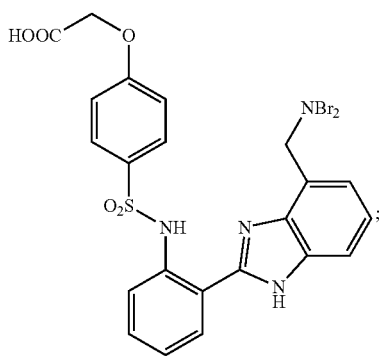

{4-{2-{4-[(methylpyridin-2-ylmethylamino)-methyl]-1H-benzimidazol-2-yl}ph-enylsulfamoyl}phenoxy} acetic acid:

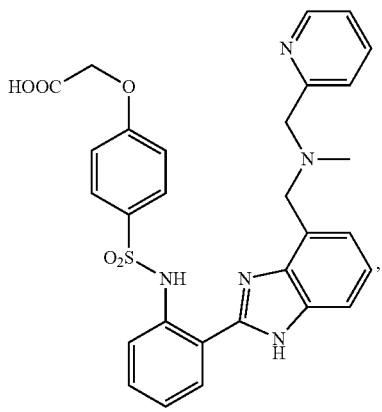 [SMILES: CN(Cc1ccccn1)Cc1cccc2[nH]c(-c3ccccc3NS(=O)(=O)c3ccc(OCC(=O)O)cc3)nc12]

and {4-{2-{4-[(bispyridin-2-ylmethylamino)methyl]-1H-benzimidazol-2-yl}phenyl sulfamoyl}phenoxy} acetic acid:

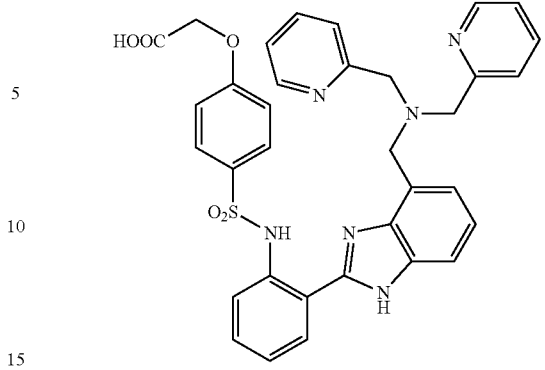

In one or more embodiments, the chemosensor used in the composition according to the invention is calcein. The selective chemosensor is associated with a cation to form a quenched chemosensor-cation complex.

The cation is preferably a transition metal, preferably chosen from $Co^{2+}$, $Cr^{2+}$, $Cu^{2+}$, $Fe^{2+}$, $Fe^{2+}$, $Mn^{2+}$, $Ni^{2+}$, $Hg^{2+}$ and $Pb^{2+}$.

More preferably still, the cation used in the composition according to the invention is $Co^{2+}$, $Cu^{2+}$, or $Ni^{2+}$.

The quenched chemosensor-cation complex is preferably chosen from:
(i) hydrophilic coumarins quenched by a metal ion, such as the following complexes: 7-(diethylamino)-2-oxo-N-((pyridin-2-yl)-methyl)-2H-chromene-3-carbox-amid-e-copper ion (Cu2+); N-(1,3-dihydroxy-2-(hydroxymethyl)propan-2-yl)-2-oxo-2H-chromene-3-carbox-amide-ferric ion (Fe3+); Calcein-ferric ion (Fe3+); calcein blue-cobalt ion (CO2+);
(ii) water-soluble benzimidazole derivatives quenched by a metal ion, such as the following complexes: N-[2-(1H-benzo[d]imidazol-2-yl)-phenyl]-N-[(E)-1-(1H-pyrrol-2-yl)methylid-ene]amine—copper ion ($Cu^{2+}$), of the following formula (II):

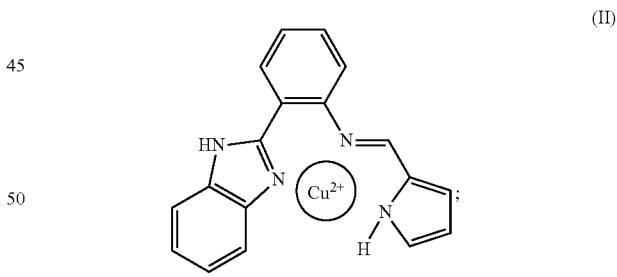
(II)

the N,S,-macrocycle of bis-benzimidazole derivative, quenched by an ion chosen from Cu2+, Fe2+, Ni2+, CO2+ and Mn2+; {4-[2-(1H-benzimidazol-2-yl)-phenyl-sulfamoyl]phenoxy} acetic acid, quenched by an ion chosen from Cu2+, Fe2+, $Ni^{2+}$, CO2+ and Mn2+; {4-{2-{4-[(diethylamino)methyl]-1H-benzimidazol-2-yl}phenylsulfamoyl}phen-oxy} acetic acid, quenched by an ion chosen from Cu2+, Fe2+, $Ni^{2+}$, CO2+ and Mn2+; {4-{2-{4-[(methylpyridin-2-ylmethylamino)methyl]-1H-benzimidazol-2-yl}phe-nylsulfamoyl}phenoxy}acetic acid, quenched by an ion chosen from Cu2+, Fe2+, $Ni^{2+}$, CO2+ and Mn2+; and {4-{2-{4-[(bispyridin-2-ylmethylamino)methyl]-1H- benzimidazol-2-yl}phenyl-sulfamoyl}phenoxy} acetic acid, quenched by an ion chosen from Cu2+, Fe2+, Ni$^{2+}$, CO2+ and Mn2+.

More preferentially still, the quenched chemosensor-cation complex is chosen from: calcein blue-cobalt ion (CO2+) and N-[2-(1H-benzo[d]imidazol-2-yl)-phenyl]-N-[(E)-1-(1H-pyrrol-2-yl)methylid-ene]amine—copper ion (Cu2+).

The composition of the invention may also comprise other compounds, which may be used in the context of biological assays, such as buffers, for example. The quenched fluorogenic compound present in the composition of the invention may be contained in a solid medium, for example a solid powder, or in a liquid medium. "Solid or liquid medium" is intended to denote a medium in solid or liquid form compatible with the sample to be tested, which is liable to contain at least one representative analyte to be detected. The fluorogenic enzymatic substrate and the quenched fluorogenic compound, which are present in the composition of the invention are preferably contained in a liquid medium for enzyme immunoassay.

Several methods exist for detecting biogenic compounds. Classical methods for detecting compounds include chromatographic techniques, such as gas chromatography, thin layer chromatography, reversed phase liquid chromatography, and liquid chromatography. Other more advanced methods for detecting biogenic amines include the use of molecular imprinted polymers (MIPs), enzymes, antibodies, single molecule, and array-based sensors.

The test can be expanded to a microfluidics device to enable rapid detection with very small amounts of test solutions as described below.

Figure 2:
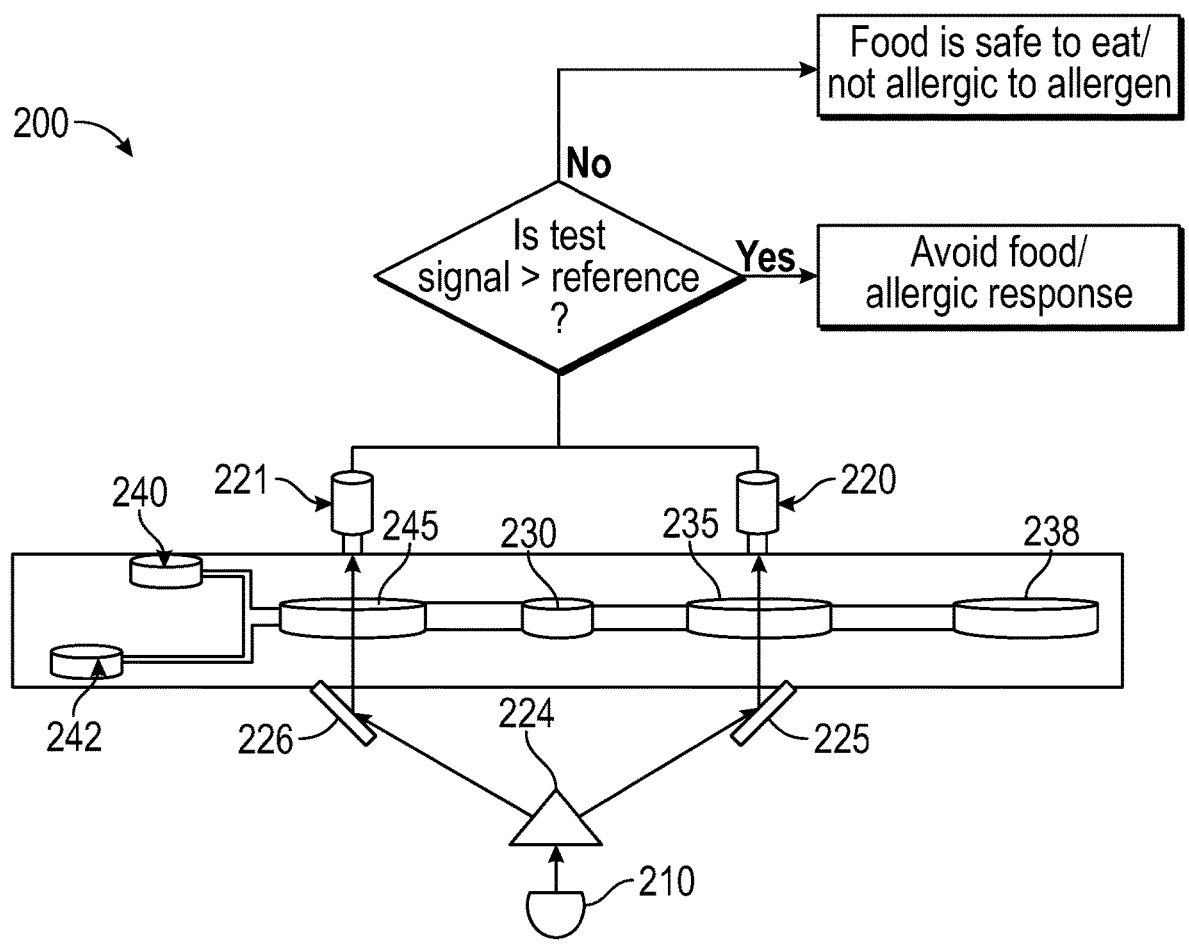
FIG. 2 illustrates an arrangement of an example microfluidics device that can be used in the present invention.

In one or more embodiments, as shown in FIG. 2, the methods of the present invention make use of a microfluidic device. In the method, a microfluidic diagnostic system 200 comprises optical modules held in a housing (not shown). It should be appreciated that portions of the housing have not been shown to enable the interior to be visible. Each optical module includes at least one light source 210 and one or more associated photodetectors 220, 221. An associated prism 224 may be used to split the light source. The light source may be directed by one or more mirrors 225, 226. A cell sample solution is added to the cell chamber 230. The cell sample solution is then directed to the reference detection chamber 245 and allergen test detection chamber 235 where light from the light source 210 is directed through the sample and then to photodetectors 220, 221 in order to measure fluorescence levels. A fluorescent probe supply 240 and an allergen solution supply 242 are directed to detection chambers 245 and 235 for measurement of the fluorescence. The fluorescence levels of the reference detection chamber 245 and allergen detection chamber 235 are compared. Sample waste can then be directed to waste chamber 238.

Fluorescent detection instruments typically use photodetectors to achieve high sensitivity detection of fluorescent emissions. Examples of such detectors include photomultiplier tubes, spectrometers, avalanche photodiodes, cooled CCD megapixel cameras and several other devices. In one or more embodiment, each of these photodetectors produce an analog signal and therefore an analog to digital converter (ADC) is required to convert the signal to a digital signal, and to ensure sufficient resolution from a sample having a low or faint analyte concentration, an ADC of the order is 16 bits or higher is often required.

In one or more embodiment, the photodetectors are light-to-frequency converters. In one or more embodiment, each of the photodetectors is also specific to test type of dye used.

If the allergen test fluorescence levels are greater than the reference fluorescence levels, then a response to an allergen is indicated and the food should be avoided. If the allergen test fluorescence levels are not greater than the reference fluorescence levels, then a response to an allergen is not indicated and the food should be safe to eat.

Using a sensitive histamine selective sensor [MIP-based sensor platforms for the detection of histamine in the nano and micromolar range in aqueous media, F. Horemans et al., Sensor and Actuators B; 148, 392-398, 2010] based on molecular imprinted polymers (MIP), capacitive biosensors [A simple capacitive biosensor device for histamine measurement, Helmi Wasoh et al., Sensor Review, 32(2), 245-250, 2012] or similar approaches [Histamine biosensor: A review, Niraj, M. M Gupta and Shweta Pandey., International Journal of Pharmaceutical Science and Research, 14, 4158-4168, 2012] would enable combining check cell solution with allergen solution as described earlier and then directly detect if histamine is produced as a positive indication of an allergic reaction.

Molecularly imprinted polymers (MIPs) are synthetic polymeric materials that possess specific cavities complimentary to the shape, size, and functional groups of a template molecule used in the imprinting process (Techniques and Instrumentation in Analytical Chemistry, in: S. Boje (Ed.) Techniques and Instrumentation in Analytical Chemistry, Elsevier 2001, pp. ii; P. Manesiotis, L. Fitzhenry, G. Theodoridis, P. Jandera, 4.20—Applications of SPE-MIP in the Field of Food Analysis, in: J. Pawliszyn (Ed.) Comprehensive Sampling and Sample Preparation, Academic Press, Oxford, 2012, pp. 457-471; L Chen, S. Xu, J. Li, Recent advances in molecular imprinting technology: current status, challenges and highlighted applications, Chemical Society Reviews, 40 (2011) 2922-2942).

Among many different synthesis pathways that can be used to create MIPs, the organic synthesis route appears to be the most popular (W. J. Cheong, S. H. Yang, F. Ali, Molecular imprinted polymers for separation science: A review of reviews, Journal of Separation Science, 36 (2013) 609-628).

The method of molecular imprinting has attracted much attention in recent years (Alexander et al. 2006, J. Mol. Recognit.; 19: 106-180). Molecular imprinting originates from the concept of creating tailor-made recognition sites in polymers by template polymerization (Mosbach K. et al., Bio/Technology, 1996, 14, 163-170; Ansell R. J. et al., Curr. Opin. Biotechnol., 1996, 7, 89-94; Wulff G. Angew. Chem. Int. Ed. Engl., 1995, 34, 1812-32; Vidyasankar S. et al., Curr. Opin. Biotechnol., 1995, 6, 218-224; and Shea K. J, Trends In Polymer Science, 1994, 2, 166-173). Molecularly imprinted polymers have demonstrated remarkable recognition properties which have been applied in various fields such as drug separation (Fischer L, et al., J. Am. Chem. Soc., 1991, 113, 9358-9360; Kempe M, et al., J. Chromatogr., 1994, 664, 276-279; Nilsson K., et al., J. Chromatogr., 1994, 680, 57-61), receptor mimics (Ramstrom O., et al., Tetrahedron: Asymmetry, 1994, 5, 649-656; Ramstrom O., et al., J. Mol. Recogn., 1996, 9, 691-696; Andersson L I., et al., Proc. Natl. Acad. Sci., 1995, 92, 4788-4792; Andersson L I., Anal. Chem., 1996, 68, 111-117) bio-mimetic sensors (Kriz D., et al., Anal. Chem., 1995, 67, 2142-2144], antibody mimics (Vlatakis G., et al., Nature, 1993, 361, 645-647), template-assisted synthesis (Bystrom S. E., et al, J. Am. Chem. Soc., 1993, 115, 2081-2083) and catalysis (Muller R., et al., Makromol. Chem., 1993, 14, 637-641; Beach J. V., et al., J. Am. Chem. Soc., 1994, Vol. 116, 379-380).

Numerous molecular imprinting-based analytical devices and methods for detection of various analytes have been reviewed by Ye and Haupt (Anal. Bioanal. Chem. 2004, 378, 1887-1897). A major challenge is to obtain an apparent signal from the polymer-analyte binding event. A variety of approaches have been proposed, yet the great majority of these involve sophisticated methods and machinery. Some examples of MIP-based sensors are as follows:

Yan et al. (U.S. Pat. No. 5,587,273) describe sensors employing molecularly imprinted film and measuring the capacitance or the light characteristics of the film after the exposing step or analyzing the film spectroscopically. MIP-based devices for detecting, analyzing and quantifying macromolecules are disclosed by Huang (U.S. Pat. No. 6,680, 210). Detection is performed by dissociating the analyte molecules from the polymer after the binding and then analyzing them.

Williams et al. (U.S. Pat. No. 6,807,842) disclose a molecular recognition sensor system for detecting the presence and concentration of an analyte including a resistive sensor having a semiconductive polymer film which swells when exposed to the analyte.

The invention also relates to methods, kits and apparatuses for the detection and determination of histamine release in response to allergens in foods, chemicals, and food additives. In one or more embodiment, the assays of the invention are capable of qualitatively and/or quantitatively measuring histamine release as a result of exposure to food. The antigens of interest are those consumed as food products or additives, i.e., allergens, which may cause chronic sensitivity and acute and chronic disease in humans and animals. Additionally, if the source of the hypersensitivity is not known, the inventive assays can quickly be adapted to screen a wide range of allergens. Another aspect of the invention relates to an assay carried out on a solid support, e.g., a dipstick. In one or more embodiment, the solid support is made of a biblious material such as nitrocellulose, for example, through which a biological fluid can migrate by capillary action.

In another aspect, the invention relates to methods, kits and apparatuses for the detection and determination of an immune response to allergens in foods, chemicals, and food additives.

In one or more embodiments, the present invention provides for a kit for evaluating the allergen sensitivity of an individual to at least one allergy comprising: at least two of the following components at least one allergen for inducing a histamine release of cells capable of releasing histamine in response to an allergen, means for detecting the histamine, at least one histamine standard, and a collection swab for buccal cells. In one or more embodiments, the cells are mast and/or basophilic and/or eosinophilic cells.

Another aspect of the present invention relates to a kit for evaluating the allergen sensitivity of an individual and/or the clinical efficacy of an allergen immunotherapy for at least one allergy comprising at least one allergen for inducing a histamine release of cells capable of releasing the histamine in response to an allergen, means for detecting histamine, and optionally at least one histamine standard.

The kit provided herein comprises at least one allergen, which can be used to induce the release of a histamine from histamine releasing cells contained in a sample. The released histamine is then detected directly. In order to accurately determine the amount of histamine in the sample (for the provision of a standard curve) a histamine standard may be optionally part of the kit.

According to one or more embodiments, the cells are mast and/or basophilic and/or eosinophilic cells.

Another aspect of the present invention relates to a kit for evaluating the allergen sensitivity of an individual or the clinical efficiency of an allergen immunotherapy for at least one allergy comprising at least two of the following components: at least one allergen for inducing a histamine release of cells capable of releasing mediators in response to an allergen, means for detecting the histamine, at least one histamine standard, and cells capable of releasing mediators in response to an allergen.

EXAMPLES

Example 1

Test solution preparation: All solutions that were used in the test were prepared in phosphate buffer saline at about pH 7 (Sigma Aldrich corporation).

Cheek cell collection: A test subject is selected to determine if a food of interest that is presented will elicit an allergic response to the subject. A swab is taken of the inside of the test subject's cheek for 30 seconds gently with a sterile cotton swab. The swab is then mixed with 10 ml phosphate buffer saline (pH 7) for 10 seconds to suspend the collected cells. This process is repeated up to 5 more times, with each time suspending the cheek cells in the same 10 ml of phosphate buffer. The suspension of cheek cells in phosphate buffer will be used for subsequent allergen tests.

Allergen solution preparation: Allergen solution was prepared by grinding the pure allergen (200-300 mg) and mixing it with 10 ml of phosphate buffer to obtain a solution of approximately 20-30 mg/ml. When testing a food having an allergen, then 400-500 mg of the food was mixed well with 10 ml of phosphate buffer such that the final solution was approximately 40-50 mg/ml. This mixture was then filtered through a syringe filter (HPF Millex, glass fiber, Low protein binding filter, from Millipore corporation).

Fluorescent probe solution preparation: The fluorescent agent to be used for the test was prepared by dissolving Calcein disodium salt (obtained from Sigma Aldrich corporation) in phosphate solution such that the final concentration was 3.1 µg/ml. Nickel chloride solution was prepared by dissolving nickel chloride (from Sigma Aldrich corporation) in phosphate buffer such that the final concentration was (6.4 µg/mL). Then, a 1:1 mixture of Calcein and nickel solution (C+N) was made that was used for subsequent testing.

A test solution of 1 ml of (C+N)+0.5 ml cheek cell sol+0.5 ml allergen solution was made. A control solution 1 ml (C+N)+0.5 ml allergen solution+0.5 ml phosphate buffer solution was made.

Fluorescence (FL) of the solutions were read on the hand-held spectrometer (PASCO scientific) that was connected to iPad or iPhone via Bluetooth.

Data was analyzed according to the following equation:

$$\% \text{ of increase over control} = [(\text{test } FL - \text{control } FL) / \text{control } FL] \times 100$$

General Methodology a. Oral swabs collected and put in buffer solution.
b. Allergen/food mixed with buffer solution and filtered.
c. Test solutions and control solutions put in cuvette.
d. Cuvette placed in hand held spectrometer.

e. Fluorescence intensity at 500 nm was measured on an iPad or an iPhone connected to the spectrometer via Bluetooth.
f. % Increase over control evaluated for test and control sample.
g. If % Increase over control is >15% it indicates a positive allergic reaction.

Test 1: 5 subjects with reported food allergies and 3 with no food allergies were evaluated. The test was run with pure allergen i.e., wheat flour, peanuts, walnuts and egg.

Figure 3:
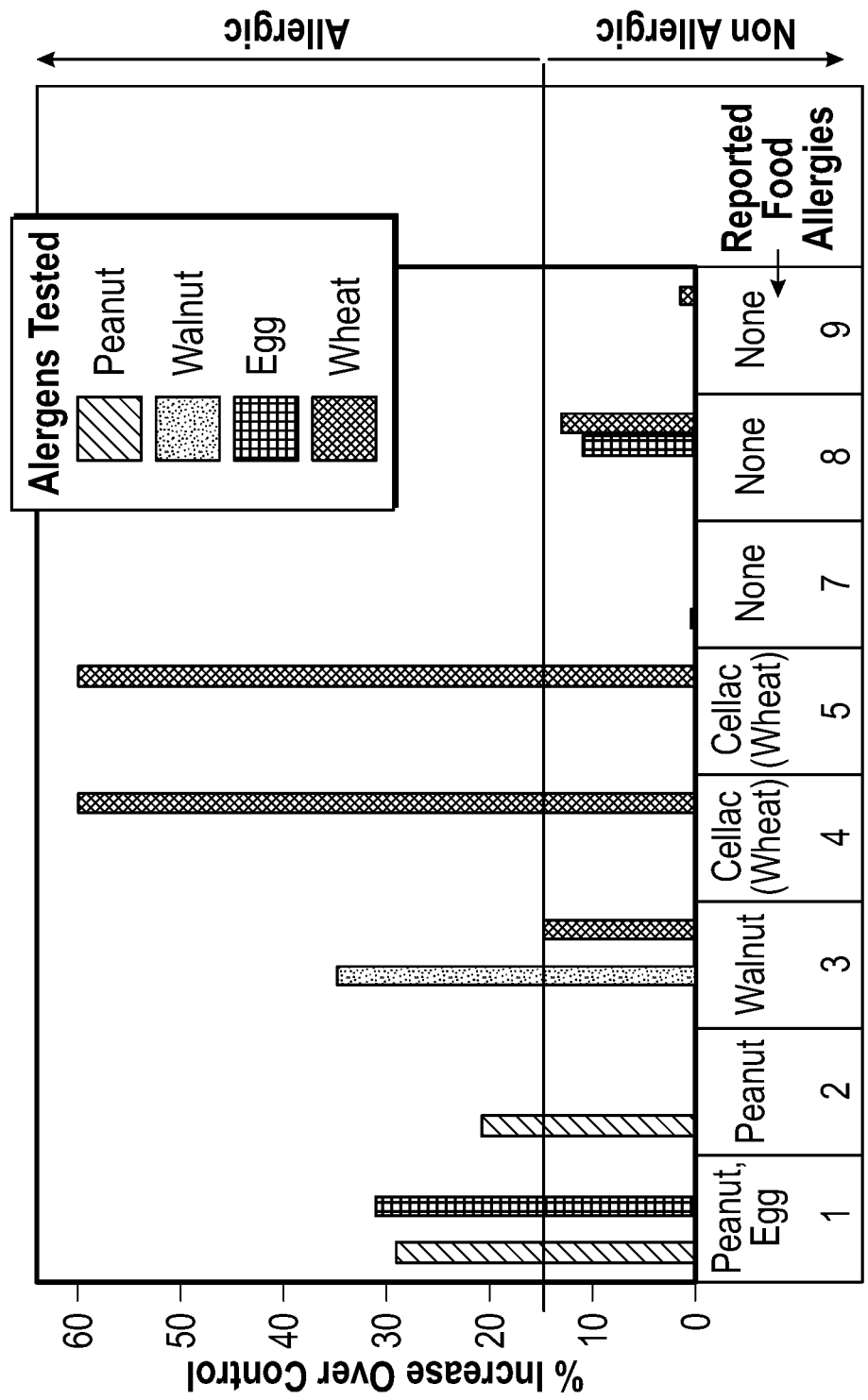
FIG. 3 is a graph showing the results of a test for histamine response showing a percent (%) increase over the control. The test was performed with 5 subjects with reported food allergies and 3 with no food allergies. The test was run with pure allergens for wheat flour, peanuts, walnuts and egg and the subjects with food allergies showed a significant increase in fluorescence over control (>15%) than the ones without allergies.

The results of Test 1 are shown in FIG. 3 and the following Table I:

TABLE I

| Subject | Allergy | Peanut | Walnut | Egg | Wheat |
|---|---|---|---|---|---|
| 1 | Peanut, Egg | 29 | | 31 | 0 |
| 2 | Peanut | 20.75 | | 0 | 0 |
| 3 | Walnut | | 34.7 | 0 | 14.08 |
| 4 | Celiac (Wheat) | | | 0 | 70.32 |
| 5 | Celiac (Wheat) | 0 | | 0 | 70.22 |
| 6 | Wheat sensitivity | 0 | | 0 | 11.12 |
| 7 | None | 0.3 | | 0 | 0 |
| 8 | None | 0 | | 10.81 | 12.81 |
| 9 | None | 0 | | 0 | 1.25 |

Observation and Conclusion: The test was able to reliably detect allergic response for subjects with peanut, egg, wheat, and walnut (tree nut) with no cross-reactivity; The test was able to distinguish allergy and non-allergy subjects and the subjects with food allergies showed a significant increase in fluorescence over control (>15%) than the ones without allergies.

Example 2

Test 2: 7 subjects with reported food allergies and 2 subjects with no allergies were evaluated by this method. The test was run with foods having the allergens. the foods with allergens that were tested were as follows: gluten—bread, peanut—butter finger bite cookies, egg—chocolate chip cookies, walnut—salted walnuts, seafood—cooked shrimp, soya—soya sauce, almond—almond butter.

Figure 4:
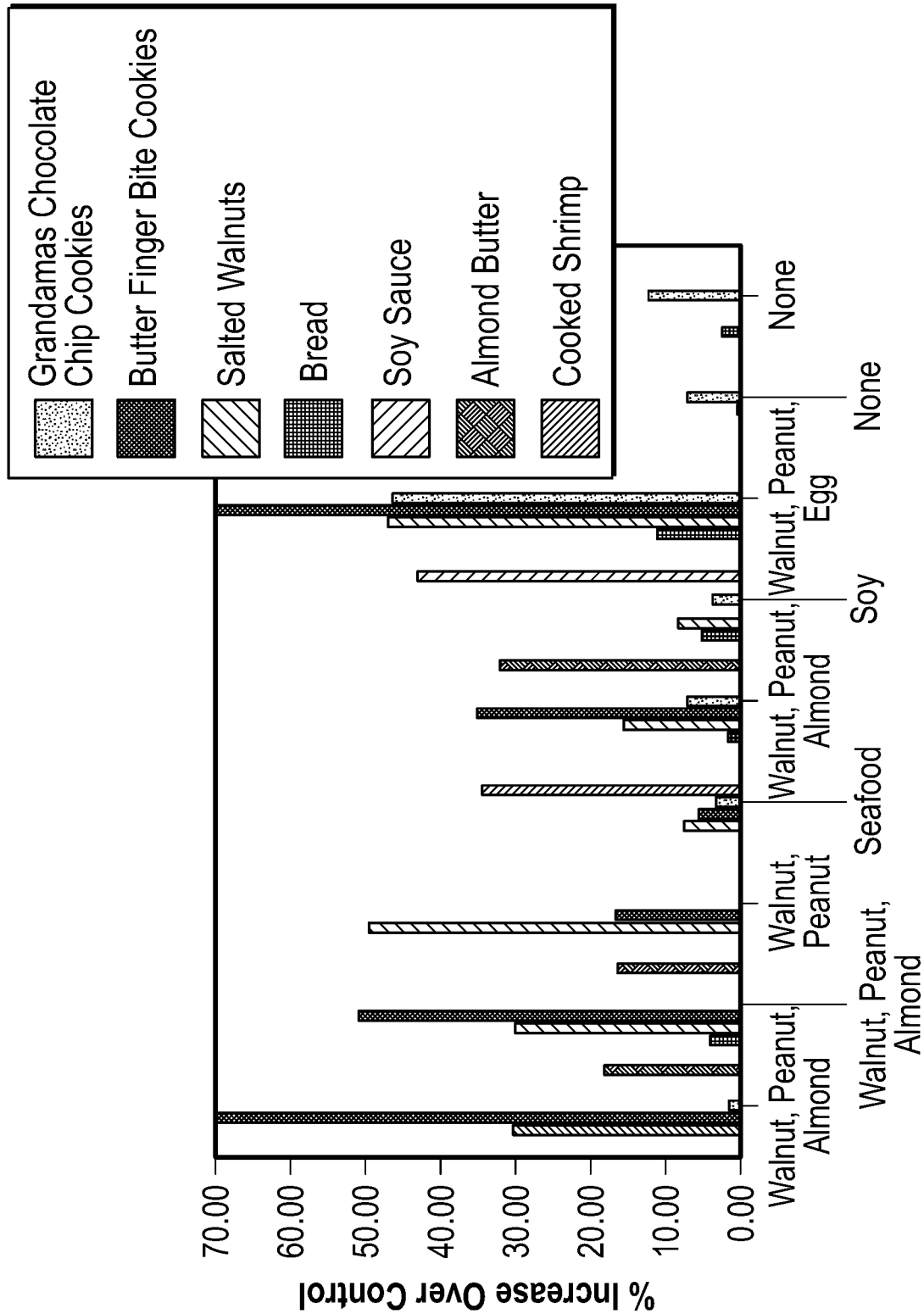
FIG. 4 is a graph showing the results of a test for histamine response showing a percent (%) increase over the control. The test was performed with 7 subjects with reported food allergies and 2 subjects with no allergies. The test was run with foods having the allergens. The foods with allergens that were tested were as follows: gluten—bread, peanut—butter finger bite cookies, egg—chocolate chip cookies, walnut—salted walnuts, seafood—cooked shrimp, soya—soya sauce, almond—almond butter. The subjects with food allergies showed a significant increase in fluorescence over control (>0.15%) than the ones without allergies.

The results of Test 2 are shown in FIG. 4 and the following Table II:

TABLE II

| Allergy | Bread | Salted Walnuts | Butter finger bite cookies | Grandmas chocolate chip cookies | Cooked Shrimp | Soy Sauce | Almond butter |
|---|---|---|---|---|---|---|---|
| Walnut, Peanut, Almond | 0.00 | 30.34 | 115.65 | 1.17 | | | 18.16 |
| Walnut, Peanut, Almond | 4.00 | 30.08 | 50.89 | 0.00 | | | 16.25 |
| Walnut, Peanut | 0.00 | 49.65 | 16.59 | 0.00 | | | |
| Seafood | 0.00 | 7.46 | 5.50 | 3.22 | 34.43 | | |
| Peanut, walnut, almond | 1.64 | 15.64 | 35.02 | 7.05 | | | 32.04 |
| Soy | 5.12 | 8.29 | 0.00 | 3.62 | | 43.08 | |
| Walnut, Peanut, Egg | 11.10 | 47.02 | 72.21 | 46.47 | | | |
| None | 0.00 | 0.00 | 0.28 | 7.09 | | | |
| None | 2.31 | 0.00 | 0.00 | 12.28 | | | |

Observation and Conclusion: The test was able to reliably detect allergic response for subjects with peanut, egg, wheat, and walnut (tree nut), almond, soya and seafood with no cross-reactivity; the test was able to distinguish allergy and non-allergy subjects; and the subjects with food allergies showed a significant increase fluorescence over control (>0.15%) than the ones without allergies.

Example 3

Figure 5:
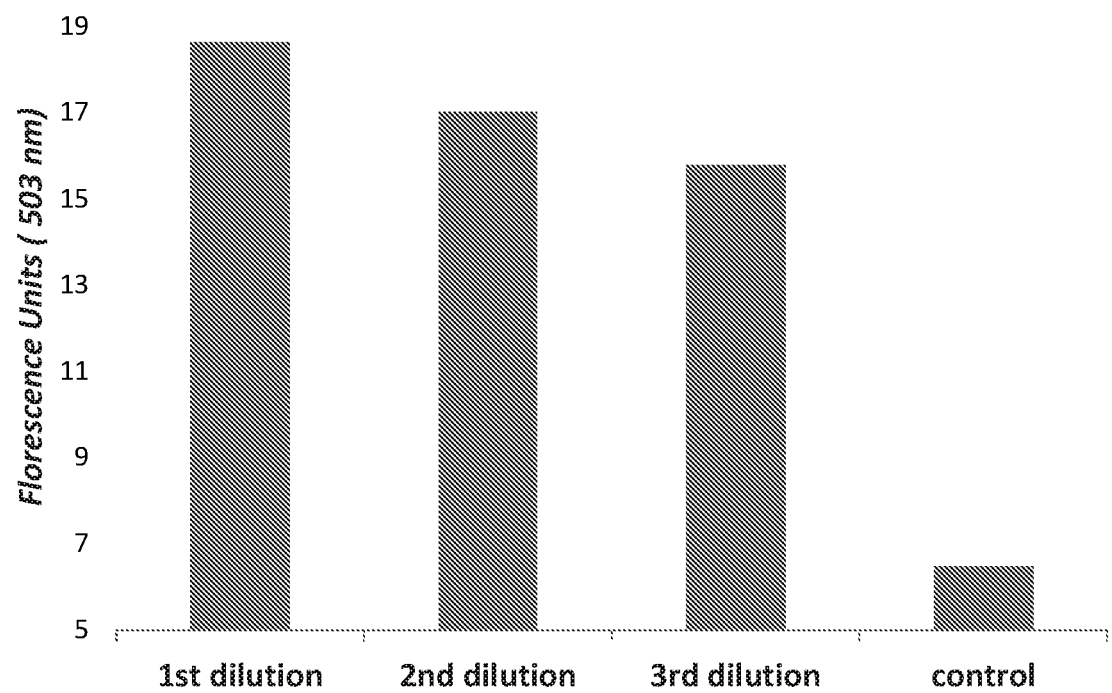
FIG. 5 is a graph showing the effects of cheek cell concentration on florescence response.

Test 3: Effect of Cheek cell concentration. Cheek swab from one subject allergic to peanut. Cheek cell solution (cc).
$1^{st}$ dilution—6 swabs in 10 ml buffer,
$2^{nd}$ dilution—1 ml of $1^{st}$ dilution diluted with 1 ml buffer
$3^{rd}$ dilution—1 ml of 2nd dilution diluted with 4 ml buffer.
Peanut solution (3 mg/ml) is used.
Test: 1 ml (C+N)+0.5 ml cheek cell solution+0.5 ml peanut solution
Controls:
Control 1: 1.5 ml buffer+0.5 ml peanut solution.
Control 2: 1 ml (C+N)+1 ml buffer.
The effects of cheek cell concentration on florescence response are shown in FIG. 5.

Observation and conclusion: Even at very low concentration of cheek cells a big response could be detected. It was also observed that the cheek cells are stable in phosphate buffer on refrigeration for at least 4 weeks and elicited a good response.

Example 4

Figure 6:
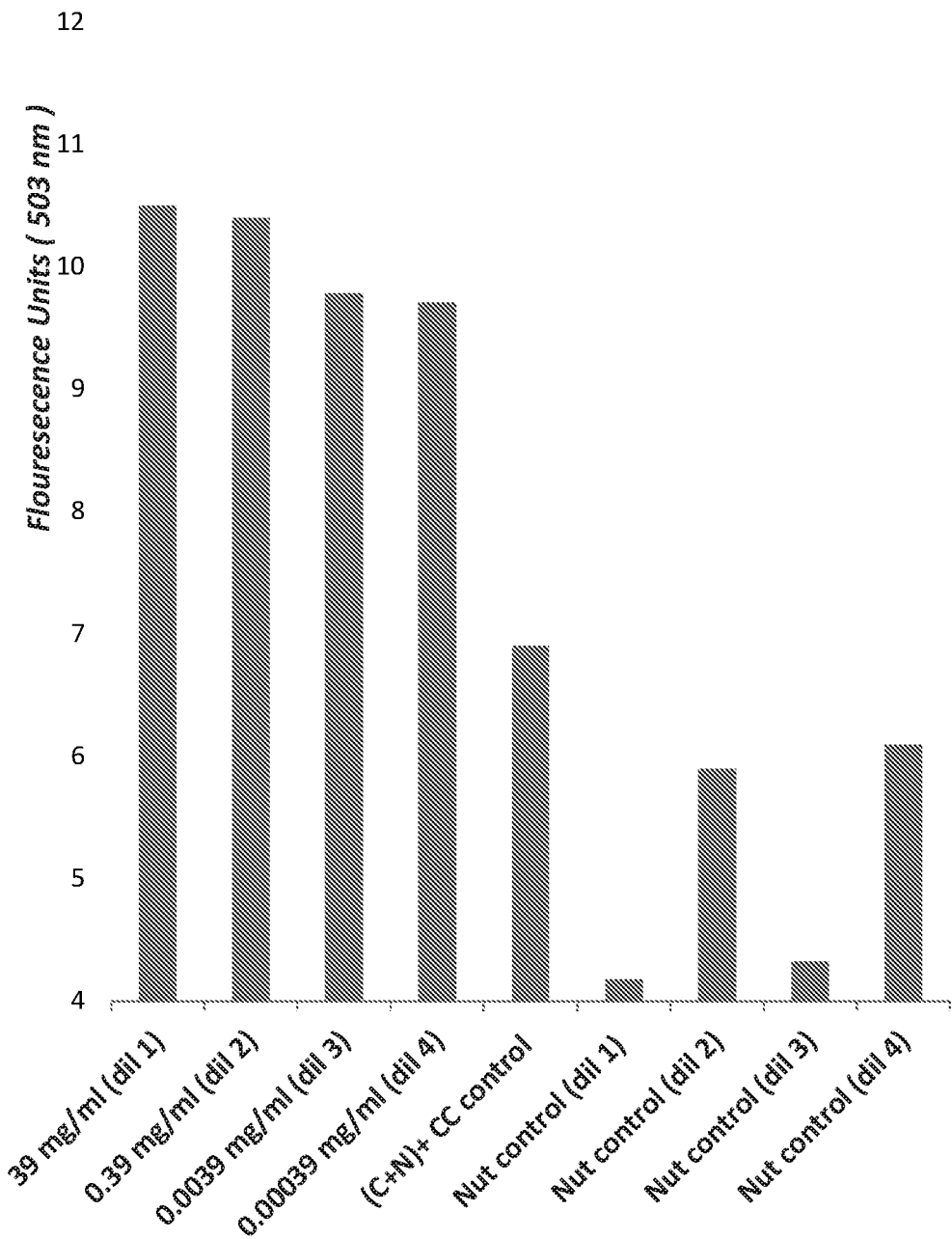
FIG. 6 is a graph showing the results of the sensitivity of detection with peanut.
Figure 7:
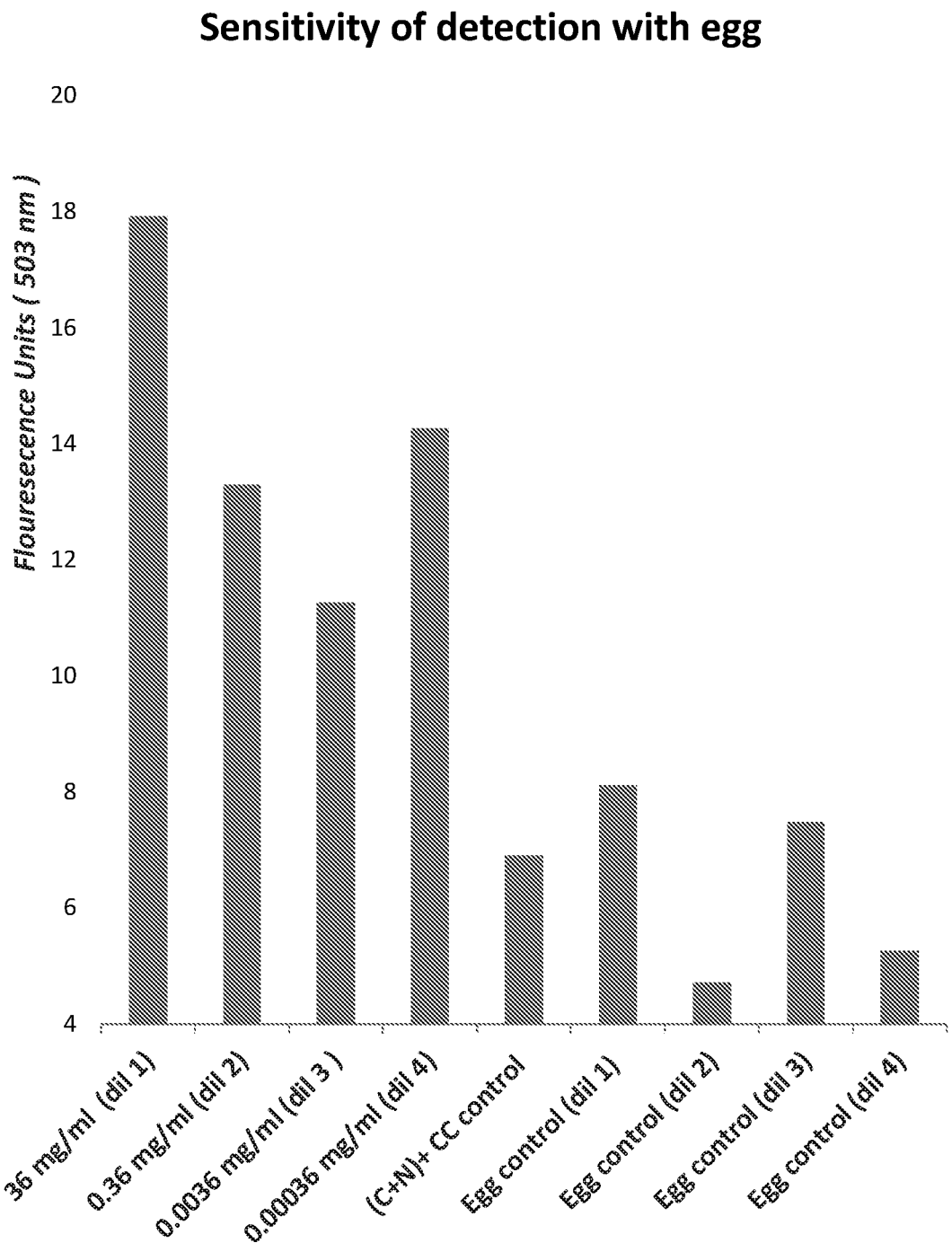
FIG. 7 is a graph showing the results of the sensitivity of detection with egg.

Test 4: Sensitivity of Detection with peanut and egg. Cheek swabs were collected from one subject who was allergic to peanuts and eggs.
Test: 1 ml (C+N)+0.5 ml cheek cells+0.5 ml peanut solution/egg solution.
Control: 1.5 ml buffer+0.5 ml peanut solution/egg solution iml (C+N)+1 ml buffer.
Sensitivity of detection with peanut is shown in FIG. 6.
Sensitivity of detection with egg is shown in FIG. 7.
Observation and conclusion: Peanut and eggs could be detected up to 390 ng/ml and 360 ng/ml Example 5

Figure 8:
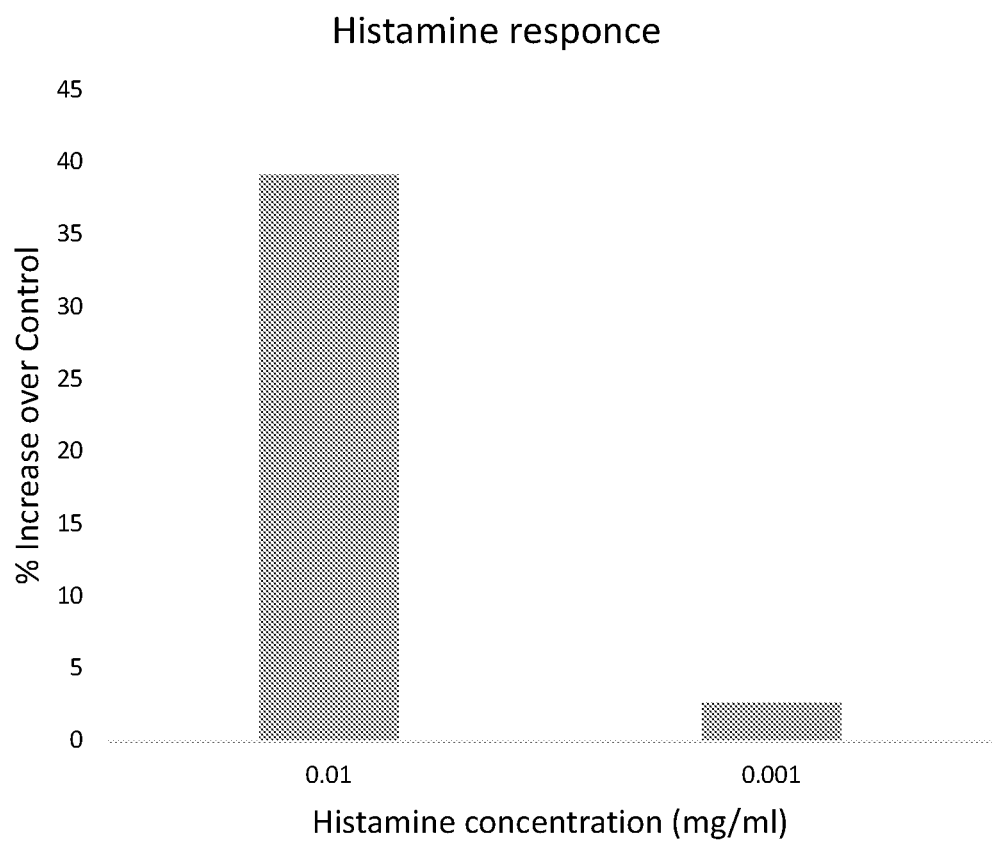
FIG. 8 is a graph showing the sensitivity of histamine detection. The response is shown with histamine standard solutions (0.01 and 0.001 mg/ml).

Test 5: Sensitivity of histamine detection.
Standard histamine solution of 0.01 and 0.001 mg/ml was evaluated by this methodology.
Test: 1 ml (C+N)+0.5 ml buffer+0.5 ml histamine
Control: 1 ml (C+N)+1 ml buffer
Response with histamine standard (0.01 and 0.001 mg/ml) is shown in FIG. 8.
Observation and Conclusion: Histamine can be detected at very low concentration of 0.001 mg/ml.

It must be noted that, as used in this specification and the appended claims, the singular forms "a," "an" and "the" include plural referents unless the content clearly dictates otherwise. Thus, for example, reference to an "agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The entire disclosures of all applications, patents and publications cited herein, if any, are herein incorporated by reference. Reference to any prior art in this specification is not, and should not be, taken as an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of the parts, elements or features.

Where in the foregoing description reference has been made to integers or components having known equivalents thereof, those integers are herein incorporated as if individually set forth.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A method for determining a presence of food allergy or food intolerance to a food in a human subject, comprising:
   (a) obtaining an isolated cheek cell sample comprising histamine-releasing cells from a human subject of interest wherein the cheek cells are obtained by a cheek swab of the subject;
   (b) obtaining a sample of food of interest comprising one or more dietary antigens;
   (c) contacting the cheek cell sample with the sample of food of interest and a histamine selective chemosensor capable of detecting a histamine response from human histamine-releasing cells;
   (d) determining a level of histamine response from the cheek cell sample obtained from the subject in response to dietary antigens of the sample of food; and
   (e) comparing the dietary antigen histamine response level determined in step (d) with normal levels of histamine in cheek cell samples,
   wherein determining the level of histamine response is accomplished using a quenched chemosensor-cation complex that forms a fluorescent compound after contact with histamine, and
   wherein higher than normal levels of histamine to dietary food antigens indicate a food allergy or food intolerance by subject of interest.

2. The method according to claim 1, further comprising determining normal baseline levels of histamine in the cheek cell sample.

3. The method according to claim 1, wherein the cheek cell sample obtained from the subject comprise cells capable of releasing histamine upon activation by exposure to or contact with an allergen of interest.

4. The method according to claim 1, wherein the cheek cell sample obtained from the subject comprise basophils or mast cells.

5. The method according to claim 1, wherein the method includes measuring a release of histamine and other mast cell or basophil products which are released upon allergen activation of mast cells and basophils.

6. The method according to claim 1, wherein the dietary antigens are derived from a food category selected from the group consisting of milk and products thereof; eggs and products thereof; meat and products thereof; fish, mollusks, and crustaceans and products thereof; oils, fats, and products thereof; grains and products thereof; pulses, seeds, kernels, peanuts, nuts, tree nuts, and products thereof; vegetables and products thereof; fruits and products thereof; sugar, sugar products, chocolate products, and confectionary; and spices and herbs.

7. The method according to claim 2, wherein the normal levels of histamine are determined by a baseline measurement of histamine from buccal cells in response to dietary antigens for individuals without symptoms relating to food allergy or food intolerance.

8. The method according to claim 7, wherein a 15% or greater increase in histamine response detected with the food antigen over the baseline level response indicates a food allergy or food intolerance to the antigen in the human subject of interest.

9. The method according to claim 1, wherein the chemosensor of the quenched chemosensor-cation complex is selected from the group consisting of hydrophilic coumarins and benzimidazole derivatives, and the cation of the quenched chemosensor-cation complex is selected from the group consisting of $Co^{2+}$, $Cr^{3+}$, $Cu^{2+}$, $Fe^{2+}$, $Fe^{3+}$, $Mn^{2+}$, $Ni^{2+}$, $Hg^{2+}$ and $Pb^{2+}$.

10. The method according to claim 9, wherein the quenched chemosensor-cation complex is selected from the group consisting of calcein blue-cobalt ion ($Co^{2+}$) complex, calcein-nickel ion ($Ni^{2+}$) complex.

11. The method according to claim 9, wherein the quenched chemosensor-ion complex is a calcein-nickel ion ($Ni^{2+}$) complex.

* * * * *